(12) United States Patent
Richter et al.

(10) Patent No.: US 10,639,432 B2
(45) Date of Patent: May 5, 2020

(54) CONTROLLABLE FLUID SAMPLE DISPENSER AND METHODS USING THE SAME

(71) Applicant: FRAUNHOFER-GESELLSCHAFT ZUR FOERDERUNG DER ANGEWANDTEN FORSCHUNG E.V., Munich (DE)

(72) Inventors: Martin Richter, Munich (DE); Sebastian Kibler, Munich (DE); Juergen Kruckow, Munich (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 225 days.

(21) Appl. No.: 14/076,152

(22) Filed: Nov. 8, 2013

(65) Prior Publication Data

US 2014/0069420 A1   Mar. 13, 2014

Related U.S. Application Data

(63) Continuation of application No. PCT/EP2011/057552, filed on May 10, 2011.

(51) Int. Cl.
*A61M 11/02* (2006.01)
*A61M 15/00* (2006.01)
(Continued)

(52) U.S. Cl.
CPC .............. *A61M 11/02* (2013.01); *A61L 9/12* (2013.01); *A61M 11/042* (2014.02);
(Continued)

(58) Field of Classification Search
CPC . A61L 9/14; A61L 9/125; A61L 9/035; A61L 9/03; A61L 9/12; A61L 2209/133;
(Continued)

(56) References Cited

U.S. PATENT DOCUMENTS

| 5,447,151 A | 9/1995 | Bruna et al. |
| 5,906,198 A | 5/1999 | Flickinger |

(Continued)

FOREIGN PATENT DOCUMENTS

| CN | 1806853 | 7/2006 |
| CN | 1959250 | 5/2007 |

(Continued)

OTHER PUBLICATIONS

Sung Bong Yang, "Application and Quality Control of Odor Measurement", retrieved from the internet on Oct. 27, 2012 from url: http://www.env.go.jp/en/air/odor/measure/02_2.pdf, Nov. 25, 2004, pp. 77-105.

*Primary Examiner* — Michael J Tsai
*Assistant Examiner* — Margaret M Luarca
(74) *Attorney, Agent, or Firm* — Michael A. Glenn; Perkins Coie LLP

(57) ABSTRACT

A fluid sample dispenser includes a microdosing device for outputting, during an activation state, a fluid sample at a fluid sample outlet to the environment, wherein the microdosing device is placeable adjacent to a person's nose so that a distance between the outlet of the microdosing device and a nostril of the person's nose is within a predefined range, and a microdosing driver unit for adjusting a dosing rate of the scent sample output at the scent sample outlet by selectively activating the microdosing device.

31 Claims, 10 Drawing Sheets

(51) Int. Cl.
*A61M 15/08* (2006.01)
*A61M 11/04* (2006.01)
*A61L 9/12* (2006.01)
*A61M 21/00* (2006.01)
*A45D 34/02* (2006.01)
*A61M 11/06* (2006.01)
*A61B 5/00* (2006.01)

(52) U.S. Cl.
CPC .... *A61M 15/0003* (2014.02); *A61M 15/0065* (2013.01); *A61M 15/0066* (2014.02); *A61M 15/08* (2013.01); *A45D 34/02* (2013.01); *A61B 5/4011* (2013.01); *A61M 11/06* (2013.01); *A61M 2021/0016* (2013.01); *A61M 2205/07* (2013.01); *A61M 2205/3368* (2013.01); *A61M 2205/3592* (2013.01); *A61M 2205/36* (2013.01); *A61M 2205/8206* (2013.01); *A61M 2209/01* (2013.01); *A61M 2209/088* (2013.01)

(58) Field of Classification Search
CPC .............. A61M 15/08; A61M 15/0065; A61M 16/0057; A61M 11/02; A61M 15/06; A61A 5/003; B05B 7/2472; A24F 47/00
See application file for complete search history.

(56) References Cited

U.S. PATENT DOCUMENTS

| | | | |
|---|---|---|---|
| 6,062,212 A | 5/2000 | Davison et al. | |
| 6,126,595 A | 10/2000 | Amano et al. | |
| 6,390,453 B1 * | 5/2002 | Frederickson | A61M 15/02 261/100 |
| 6,890,304 B1 | 5/2005 | Uebaba et al. | |
| 7,727,181 B2 | 6/2010 | Rush | |
| 2002/0036358 A1 * | 3/2002 | Watkins | A61L 9/122 261/26 |
| 2003/0206834 A1 * | 11/2003 | Chiao | A61L 9/014 422/124 |
| 2005/0121023 A1 | 6/2005 | Braithwaite | |
| 2005/0123420 A1 * | 6/2005 | Richter | F04B 43/046 417/413.2 |
| 2005/0269374 A1 | 12/2005 | Koerner et al. | |
| 2006/0144956 A1 * | 7/2006 | Ruetz | A61L 9/035 239/34 |
| 2007/0023540 A1 * | 2/2007 | Selander | A61L 9/122 239/34 |
| 2007/0166185 A1 * | 7/2007 | Bartels | A61L 9/14 422/5 |
| 2009/0126722 A1 | 5/2009 | Sugita et al. | |
| 2009/0196587 A1 * | 8/2009 | Cheung | A61L 9/037 392/394 |
| 2009/0216070 A1 * | 8/2009 | Hunt | H04N 5/775 600/27 |
| 2010/0089395 A1 | 4/2010 | Power et al. | |

FOREIGN PATENT DOCUMENTS

| | | |
|---|---|---|
| EP | 1562094 | 8/2005 |
| GB | 2144997 | 3/1985 |
| JP | S62-21353 U | 2/1987 |
| JP | 08-502689 | 3/1996 |
| JP | 08-299441 | 11/1996 |
| JP | 10-085315 | 4/1998 |
| JP | 2003260122 | 9/2003 |
| JP | 2004267888 | 9/2004 |
| JP | 2005111041 | 4/2005 |
| JP | 2006198201 | 8/2006 |
| JP | 2007503971 | 3/2007 |
| JP | 2007136451 | 6/2007 |
| JP | 2007289298 | 11/2007 |

* cited by examiner

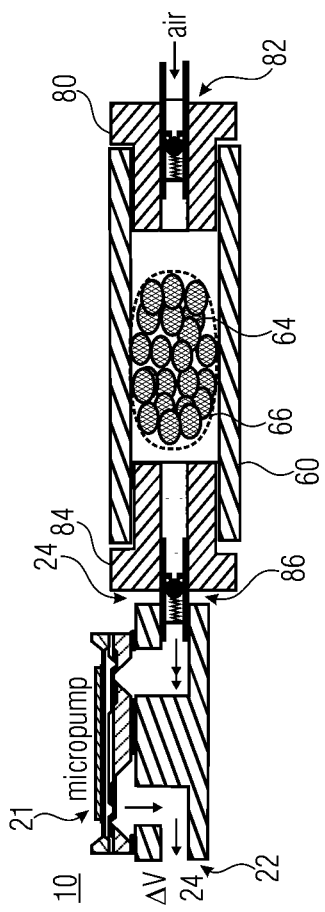
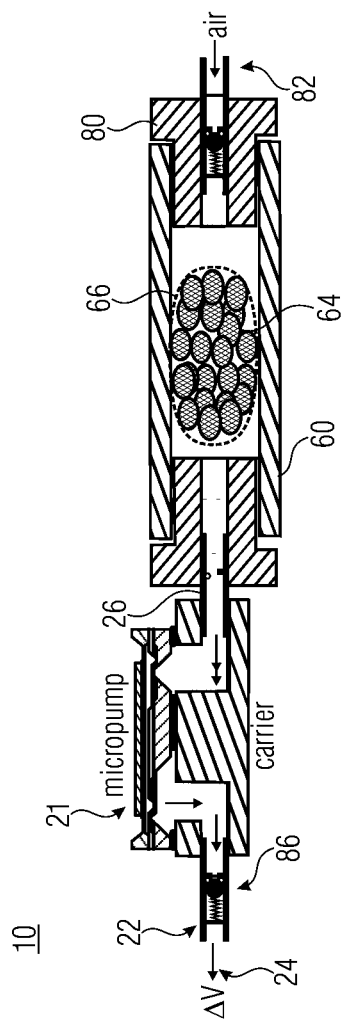

CONTROLLABLE FLUID SAMPLE DISPENSER AND METHODS USING THE SAME

CROSS-REFERENCE TO RELATED APPLICATIONS

This application is a continuation of copending International Application No. PCT/EP2011/057552, filed May 10, 2011, which is incorporated herein by reference in its entirety.

BACKGROUND OF THE INVENTION

The present invention relates to a controllable fluid sample dispenser and the use of the controllable fluid sample dispenser for supplying a fluid sample with a predefined and precise dosing rate to a person's nose. In particular, the present invention relates to a fluid sample dispenser for controllably dispensing or applying a scent, aroma, flavor sample or a medical or pharmaceutical agent to a person utilizing the inventive controllable fluid sample dispenser. Thus, the present invention generally relates to the field of precisely dispensing or applying any fluid sample, specimen or assay to the respiratory system of a person/user. Moreover, the present invention relates to a method for determining the minimum concentration of a fluid sample a person can detect and, further, to a method for determining the fluid sample detection limit of a fluid detection means.

Known scent delivery systems are configured for providing a specific scent to whole rooms. Therefore, known scent delivery systems are relatively bulky for providing a sufficiently intensive scent impression in rooms, shopping malls, wellness areas, car interiors and so on. However, these known systems have the drawback that every person in the scent provided room will be treated with the fragrance by breathing.

SUMMARY

According to an embodiment, a fluid sample dispenser may have: a microdosing device fluidically coupled to a fluid sample reservoir and a fluid sample outlet, the microdosing device being configured to create, during an activation state, a flow of a carrier gas through the fluid sample reservoir for taking up particles of the fluid sample into the carrier gas, and to output a fluid sample in form of the carrier gas with the fluid sample particles at the fluid sample outlet to the environment, and a microdosing driver unit for adjusting a dosing rate of the fluid sample output at the fluid sample outlet by selectively activating the microdosing device.

Another embodiment may have the use of the inventive controllable fluid sample dispenser for selectively supplying a fluid sample with a predefined dosing rate to a person's nose.

According to another embodiment, a method for determining the minimum scent concentration of a scent sample a person can detect may have the steps of: setting or calibrating the scent concentration of the scent sample provided by the scent reservoir, supplying the scent sample with a start dosing rate to the person's nose, increasing the dosing rate supplied to the person's nose, until the person senses the scent sample, wherein the minimum scent concentration detectable by the person corresponds to the currently supplied dosing rate, when the person senses the supplied scent sample.

According to another embodiment, a method for determining the scent sample detection limit of a person may have the steps of: setting or calibrating the concentration of the scent sample provided by the scent reservoir, supplying the scent sample with a start dosing rate to the person's nose, decreasing the dosing rate supplied to the person's nose, until the person stops to sense the scent sample, wherein the scent sample detection limit of the person corresponds to the currently supplied dosing rate, when the person stops to respond to or to sense the supplied scent sample.

According to another embodiment, a method for determining the minimum scent concentration of a scent sample a scent detection means can detect may have the steps of: setting or calibrating the scent concentration of the scent sample provided by the scent reservoir, supplying the scent sample with a start dosing rate to a sensing element of the scent detection means, increasing the dosing rate supplied to the sensing element, until the scent detection means responds to the scent sample, wherein the minimum scent concentration detectable by the scent detection means corresponds to the currently supplied dosing rate, when the scent detection means responds to the supplied scent sample.

According to another embodiment, a method for determining the scent sample detection limit of a scent detection means may have the steps of: setting or calibrating the concentration of the scent sample provided by the scent reservoir, supplying the scent sample with a start dosing rate to a sensing element of the scent detection means, decreasing the dosing rate supplied to the sensing element, until the scent detection means stops to respond to the scent sample, wherein the scent sample detection limit of the scent detection means corresponds to the currently supplied dosing rate, when the scent detection means stops to respond to the supplied scent sample.

According to another embodiment, a fluid sample dispenser may have: a microdosing device fluidically coupled to a fluid sample outlet, the microdosing device being configured to create, during an activation state, a flow of a carrier gas to the fluid sample outlet; a fluid sample supply means fluidically coupled to a fluid sample reservoir, the fluid sample supply means being configured to selectively supply particles of the fluid sample from the fluid sample reservoir into the carrier gas flowing to the fluid sample outlet; and a microdosing driver unit for adjusting a dosing rate of the fluid sample output at the fluid sample outlet by selectively activating the microdosing device and/or the fluid sample supply means.

The present invention is based on the finding that a fluid sample dispenser can apply or dispense very small quantities with very high precision of fluid samples, such as a scent sample, aroma sample, flavor sample and/or a medical or pharmaceutical agent, to a single person with a very high reliability by bringing a predefined quantity per time unit of a specific fluid sample in immediate proximity to the nose or naris (nostril) of the person to be provided with the fluid sample.

According to the inventive concept, a fluid sample dispenser comprises a microdosing device fluidically coupled to a fluid sample reservoir and a fluid sample outlet, the microdosing device being configured to create during an activation state, a flow of a carrier gas (i.e. a carrier gas stream) through the fluid sample reservoir for taking up particles (e.g. in form of molecules, liquid droplets and/or fine solid particles) of the fluid sample into the carrier gas, and to output a fluid sample in form of the carrier gas with the fluid sample particles at the fluid sample outlet to the environment. A microdosing driver unit is configured to adjust the dosing rate of the fluid sample output at the fluid sample outlet by selectively activating the microdosing device. Alternatively, the fluid sample dispenser may again comprise a microdosing device fluidically coupled to a fluid sample outlet, wherein the microdosing device is configured to create, during an activation state, a flow of a carrier gas (i.e. a carrier gas stream) to the fluid sample outlet. The fluid sample dispenser further comprises a fluid sample supply means fluidically coupled to a fluid sample reservoir. The fluid sample supply means is configured to selectively supply particles or molecules or droplets of the fluid sample from the fluid sample reservoir into the carrier gas flowing to the fluid sample outlet. A microdosing driver unit is configured to adjust the dosing rate of the fluid sample (in form of the fluid sample particles in the carrier gas) output at the fluid sample outlet by selectively activating the microdosing device and, if necessitated, by selectively activating the fluid sample supply means. The fluid sample supply means may comprise an active fluid supply element, e.g. a further micropump having a pump chamber providing a predefined stroke volume, or a passive fluid supply element.

Thus, according to both alternatives of the inventive fluid sample dispenser, fluid sample particles or molecules or droplets stored in a fluid sample reservoir are provided to a carrier gas, wherein, for example, the carrier gas is sucked in from the environment and filtered by an adequate filter element. According to the first alternative, the flow of the carrier gas is guided through the reservoir so that the carrier gas can take up the particles of the fluid sample stored in the reservoir. Alternatively, the particles of the fluid sample can be selectively injected from the fluid sample reservoir into the flow of the carrier gas by means of an additional (active or passive) fluid sample supply means.

In order to supply the fluid sample with a very precise and accurate dosing rate to the person's nose, the outlet of a microdosing device, which may be implemented for example by means of a micropump, micro-membrane pump or micro fan, is fixed to a person's head so that a distance between the outlet of the microdosing device and a nostril of the person's nose is within a predefined range having a possible extension of 0 to 5 cm. Alternatively, the fluid sample may be directly supplied into the nostril of the person's nose by placing the outlet of the microdosing device, for example over a tubing element, i.e. by inserting the outlet of the tubing element into the nostril of the person's nose.

Due to the very high dosing precision of micro-membrane pumps available at present, a dosing precision of the fluid sample with minute volume quantities, such as, for example, 1 nl to 10 µl are achievable per pump stroke.

By supplying the fluid sample to the person with a very high dosing accuracy and with very precisely definable time intervals or periods, a very effective fluid sample dispenser arrangement can be realized. Moreover, the microdosing driver unit for selectively activating the microdosing device may be implemented for receiving the control signals from a remote system controller, for example from a computer, a video game console (e.g. in form of an interactive entertainment computer), or any platform with an audio and/or visual media playing functionality. The inventive fluid sample dispenser may be implemented within or attached to a headset. Moreover, a wired connection may be implemented, for example, in a signal line connected to the remote system controller or, alternatively, the signal receiving element of the microdosing driver unit may be configured to install a wireless connection to the remote system controller.

Thus, the inventive fluid sample dispenser may implement a scent dosing system which delivers a defined quantity of scent to the nose of single user. By breathing these scent molecules, the user has a specific scent impression. Alternatively, a medical or pharmaceutical agent may be very precisely supplied/applied to the respiratory system of a person to be medically treated with a precise dosing rate. Moreover, the sensitivity of a test person to smell or taste a scent, a fragrance, an aroma etc. can be very precisely checked (e.g. by a medical examiner) using the inventive fluid sample dispenser.

The inventive solution for a single person scent delivery achieves a number of benefits and advantages when compared to known scent dispenser arrangements, e.g. in form a whole room fragrance dispenser. Using a single person scent dispenser, each person can decide to be treated by a scent, fragrance etc. or not to be treated. Other persons in the room will not smell any fragrance, so that the resulting acceptance for a user of the inventive fluid sample dispenser will be very high.

Using the inventive single person fluid sample dispenser which delivers a very small amount of the fluid sample (e.g. a scent, etc) with a very high dosing accuracy and within very precisely definable timing intervals or periods, the scent impression can be controlled to appear only for short intervals as the scent impression will disappear immediately within a few seconds by diffusion. Thus, after a few seconds the user cannot smell the old (previously supplied) scent anymore. Now, a new (e.g. different) scent can be delivered to the user. Moreover, the intensity of the supplied fluid sample may be easily adjusted or adapted. In connection with audio and video applications, the inventive fluid sample dispenser enables new applications for games, learning and training applications, mobile phones, medical diagnostics and applications (e.g. via the respiratory system), warning scents in cars, and more.

According to the inventive fluid sample dispenser, a sufficiently powerful microfluidic actuator may pump a gaseous medium (air and scent), from a reservoir with a scent source comprising or providing the scent molecules, in immediate proximity to the user's nose as the flow rate of the microfluidic actuator is strong enough to carry the fluid molecules outside the reservoir directly to the outlet of the microdosing device and to the nostril of the user's nose.

As already indicated, according to the inventive single person scent delivery, a very small and precisely defined quantity of scent can be delivered to a person's nose. Based on the inventive utilization of sufficiently powerful microfluidic actuators, the inventive fluid sample dispenser can realize a scent dosing system with a very tightly closed housing, which reliably avoids malfunctioning smells and which is very bubble tolerant, so that any bubbles supplied from the fluid reservoir will not make the dosing system fail.

Due to the very small achievable dimensions of the powerful microfluidic actuators, as utilized in the context of the present invention, the inventive fluid sample dispenser may be easily attached to or integrated into a headset. Thus, the present invention provides a reliable microdosing system, which is small enough to be arranged nearby to the user's nose, e.g. in the mouthpiece of a headset, and which can deliver a defined small amount of a fluid sample directly to the user's nose. Thus, the inventive fluid sample dispenser or scent dosing system can use high performance micropumps achieving a pumping rate up to 350 ml/min with air, and a back pressure ability of 25 kPa. Even small silicon micropumps with a chip size of e.g. 7×7×1 mm$^3$ achieve gas pump rates of up to 40 ml/min. Next, with peristaltically driven plastic micropumps, pump rates of up to 30 ml/min are achievable. With that, using new and powerful micropumps, it will be possible to transport the fluid sample molecules dissolved in air directly via an outlet of the microdosing device through the air, e.g. over a distance of up to about 10 cm or more, to the user's nose.

Next, at the outlet of the dispenser a nozzle with a diameter between e.g. 5 μm and 100 μm can be arranged, to increase the flow velocity of the scent/air sample flow to bridge the gap between fluid sample outlet and the user's nose.

Corresponding to the utilization of a fluid sample in form of scent molecules, other samples, specimens or assays may be applied or dispensed, e.g. in form of medical or pharmaceutical agents, to the user's nose and, thus, to the respiratory system of the user.

BRIEF DESCRIPTION OF THE DRAWINGS

Embodiments of the present invention will be detailed subsequently referring to the appended drawings, in which:

FIGS. 2a-i show principle illustrations of different realizations of a fluid sample dispenser in accordance with another embodiments of the present invention;

DETAILED DESCRIPTION OF THE INVENTION

Before discussing the present invention in further detail using the drawings, it is pointed out that in the figures identical elements and elements having the same functionality and/or the same effect are provided with the same reference numbers so that the description of these elements and of the functionality thereof illustrated in the different embodiments is mutually exchangeable or may be applied to one another in the different embodiments.

Subsequently, a first general embodiment of a fluid sample dispenser 10 for supplying, during selected time intervals, a fluid sample with a precisely adjusted dosing rate to the immediate proximity of a user's nose or nostril will be described using FIGS. 1a-c for a general discussion of their functional context.

Figure 1A:
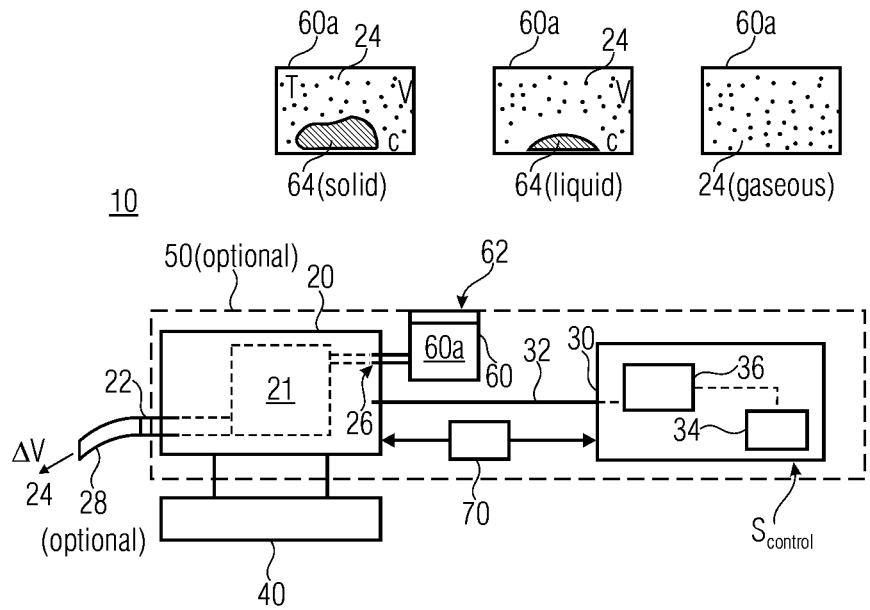
FIGS. 1a-c show principle illustrations of the functional groups of the fluid sample dispenser in accordance with embodiments of the present invention.

As depicted in FIG. 1a, the "remote" controllable fluid sample dispenser 10 comprises a microdosing device 20 having a fluid sample outlet 22, a microdosing driver unit 30 at least electrically and, as an option, mechanically coupled to the microdosing device 20, and a fixing element 40. As an optional measure, FIG. 1a shows a common housing 50 for the microdosing device 20 and the microdosing driver unit 30, wherein the fixing element is, in the case of the presence of the common housing 50, attached to the common housing 50. It should become clear that the microdosing device 20 and the microdosing driver unit 30 may also be implemented as separate functional groups and may be housed in different housings (not shown in FIG. 1a). In this case, at least the fixing element 40 is attached to the microdosing device 20. The microdosing device 20 comprises a fluid sample outlet 22 for outputting, during an activated state of the microdosing device 20, a fluid sample 24 to the environment. The microdosing driver unit 30 is configured for adjusting a dosing rate of the fluid sample 24 output at the fluid sample outlet 22 by selectively activating the microdosing device 20. Thus, the microdosing driver unit 30 may be connected by means of a control line 32 with the microdosing device 20 for providing electrical control signals to the microdosing device 20.

Optionally, the microdosing driver unit 30 may be configured or programmed, e.g. for a stand alone configuration without a remote system controller, in order to supply the fluid sample 24 output at the fluid sample outlet 22 in a continuous or intermittent (sporadic) manner or within defined time intervals.

Moreover, a fluid sample reservoir 60 may be fluidically coupled to an inlet 26 of the microdosing device 20. The optional reservoir 60 may be located externally or internally into the microdosing device 20. Moreover, the fluid sample reservoir 60 may for example comprise an elastic/resilient sidewall so that no negative pressure arises during emptying, and optionally has a septum and/or an inlet port (not illustrated in FIG. 1a) for filling or refilling the reservoir 60 with the fluid sample or a fluid sample creating material 64. Moreover, the reservoir 60 may be implemented as fluid channel separated by means of a filter element 62 from the environment, wherein the fluidic channel comprises, for example, a piece of the fluid sample creating material so that fluid sample molecules are dissolved in a gas, for example air, provided through the filter element 62 from the environment.

The storage volume 60a of the reservoir 60 may comprise a solid material as the fluid sample carrier 64. Based on the active surface of the fluid sample carrier 64, the temperature T in the fluid sample reservoir 60, the fluid sample carrier 64 will dispense fluid sample molecules to the inner volume 60a of the fluid sample reservoir 60 until an equilibrium concentration c of the fluid sample 24 in form of fluid sample molecules dissolved in a gas will be present in the inner volume of the fluid sample reservoir 60. Thus, a defined concentration c (c=N/V with N is the amount of molecules, and V is the value of the inner space 60a) of the fluid sample 24 is adjustable within the inner volume 60a of the fluid sample reservoir 60. The concentration c can be adjusted (e.g. increased or decreased) by changing (e.g. increasing or decreasing) the temperature of the fluid sample carrier or the fluid sample (respectively a solid sample material) with a heater element (for increasing the temperature) or cooling element (for decreasing the temperature). As a further alternative, a predefined concentration of the fluid sample 24 may be achieved within the inner volume of the fluid sample reservoir 60 by arranging a fluid sample carrier 64 having a liquid phase and a predefined mass. After heating the fluid sample carrier 64, all molecules of the fluid sample will be in a gaseous phase for achieving a specific, predefined concentration c of the fluid sample within the inner volume 60a of the fluid sample reservoir 60. In order to avoid a recondensation of the fluid sample at the walls of the reservoir, the walls of the reservoir 60 should be heated to a wall temperature exceeding a recondensation temperature of the fluid sample. Thus, a predefined amount of molecules of the fluid sample is within the inner volume of the fluid sample reservoir 60. To summarize, based on the quantity (or volume) of the fluid sample carrier 64 and the resulting surface thereof effective for emitting or dispensing fluid sample particles to the inner volume 60a of the reservoir 60, the concentration c of fluid sample particles in the inner volume 60a is precisely adjustable to a desired, predefined concentration value c.

With that, the concentration c of the scent particles, molecules or droplets is known or can be detected and/or adjusted principally. Based on a precise microdosing element (e.g. a micropump with a stoke volume ΔV) which can transport a defined volume from the fluid sample reservoir, a precise and accurate dosing of a fluid sample, e.g. a scent, to the nose of a person can be realized.

Due to the minute dead volume of the microdosing device 20 used for the inventive fluid sample dispenser 10, the fluid sample can be supplied to the environment (e.g. the user's nose) immediately (i.e. essentially without any delay) after a received activation signal and, also, with a very precise dosing rate. For example, the (approximate) number $N_1$ of fluid sample particles supplied to the environment can be calculated and, thus, adjusted as follows: $N_1=c*n*\Delta V$, wherein "c" is the concentration of the fluid sample particles in the reservoir (and, respectively, in the carrier gas at the fluid sample outlet), wherein "ΔV" is the stroke volume of the micropump of the microdosing device 20, and wherein "n" is the number of pump strokes or diaphragm excursions for transporting the carrier gas in a predetermined direction.

The fluid sample present in the inner volume of the fluid sample reservoir 60 may comprise a scent sample, an aroma sample, a flavor sample and/or a sample of a medical or pharmaceutical agent. Thus, the fluid sample creator may be a solid body (solid state material) or a liquid material for providing the fluid sample molecules to the inner volume of the fluid sample reservoir 60. In case the fluid creating material is a solid body or a solid state material, the provision of the fluid sample molecules in the inner volume of the fluid reservoir 60 may be achieved by releasing particles or molecules or droplets of a substance from or through a surface of a solid body or solid state material containing the substance (e.g. due to the desorption phenomenon). In case the fluid sample creating material 64 is present in form of a liquid material, the liquid material may be vaporized by heating to provide the defined concentration of fluid sample molecules in the inner volume of the fluid sample reservoir 60. Moreover, as a further alternative, the fluid sample molecules may be present already in a gaseous form with a defined concentration c within the inner volume of the fluid sample reservoir 60. Thus, the fluid sample reservoir 60 can be a (fixed or replaceable) fluid sample container or cartridge.

In the context of the present invention, it is described that particles or molecules of the fluid sample are supplied to the carrier gas to form the fluid sample which is output at the fluid sample outlet to the environment. It should become clear that the term "particles" usually refers to (e.g. microscopic) particles of sizes ranging from atoms to molecules or groups/clusters of molecules. For example, the carrier gas having taken up or dissolved therein the fluid sample particles can also be referred as an "aerosol" which is a suspension of fine solid particles or liquid droplets in a gas or carrier gas, wherein the carrier gas is, for example, filtered air supplied from the environment. Thus, the term particles is used synonymously for liquid droplets, molecules and/or fine solid particles of the fluid sample in the present specification.

Moreover, FIG. 1a shows some exemplary illustrations of the inner volume 60a of the reservoir 60 filled with the fluid sample 24.

The filter element 62 may be an active carbon filter. The filter element 62 may filter out potential contaminations or other undesired substances from the environment and may also prevent molecules of the fluid sample 24 from leaking from the inner volume of the reservoir 60 to the environment. In order to avoid an uncontrolled flow of the scent sample from the reservoir 60 through the microdosing device 20 to the outlet 22, a so called free flow protection element (not shown in FIGS. 1a-c) may be arranged in the fluid channel downstream to the fluid sample reservoir 60. The free flow protection element may be, for example, implemented as a check valve e.g. in form of a pre-tensioned diaphragm. To summarize, the fluid sample reservoir 60 may be configured to provide the fluid sample 24 to the microdosing device 20 with a specific fluid sample concentration in the form of a fluid sample molecules dissolved in filtered air.

Moreover, the fluid sample reservoir may comprise a plurality of separated volumes (not shown in FIGS. 1a-c) for storing different fluid samples. The different fluid samples may be selectively suppliable to the microdosing device by activating a switching element (not shown) for connecting one of the plurality of separate volumes with the microdosing device 20. Alternatively, the microdosing device may comprise a plurality of micropumps of micro fans (not shown), wherein each of the plurality of micropumps or micro fans is associated to a different volume of the plurality of separated volumes of the fluid sample reservoir. Moreover, the microdosing driver unit 30 may be configured to selectively and/or alternatively activate each of the plurality of micropumps or micro fans each being associated to a different volume of the plurality of separated volumes of the fluid sample reservoir 60.

As shown in FIG. 1a, the fluid sample reservoir is arranged, in the (desired) flow direction of the fluid sample 24, upstream to the microdosing device 20, wherein an inlet 26 of the microdosing device 20 is fluidically coupled to an outlet of the fluid sample reservoir 60. The fluid sample reservoir 60 may be removably connected to the microdosing device 20. Alternatively, the fluid sample reservoir 60 may be permanently attached to the microdosing device 20, so that the microdosing device 20 and the fluid sample reservoir 60 may be arranged in the same housing (or substrate) 50.

Moreover, at least one of the inlet of the fluid sample reservoir 60, the outlet of the fluid sample reservoir 60, the inlet of the microdosing device 20 and the outlet of the microdosing device 20 may comprise the free flow protection element, e.g. in form of a check valve, for preventing an undesired flow of the fluid sample in a flow direction opposite to the intended flow direction of the fluid sample 24. As already outlined above, the microdosing device 20 may comprise a micropump 21 with a pump chamber providing a stroke volume ΔV. In micro-membrane or micro-diaphragm pumps, the membranes or diaphragms (micro-membranes or micro-diaphragms) are driven by a predetermined or adjustable pump stroke or diaphragm excursion for transporting the fluid sample in a predetermined direction. For example, a piezoelectric element, which may be enabled electrically may exemplarily be used as a micropump or micro-membrane pump of the microdosing device 20. Depending on the electrical excitation, the stroke volumes of micro-membrane or micro-diaphragm pumps may exemplarily be generated in a range from 1 nl to 10 µl (or more) per pumping stroke.

In order to achieve a high dosing precision of the fluid sample 24 when supplying the fluid sample 24 to the immediate proximity of the user's nose, the so called dead volume of the micropump should be as low as possible. The dead volume of the micropump extends between an exit of the pump chamber 21 and the outlet 22 of the micropump 20. Thus, for achieving a high precision, the dead volume of the micropump of the microdosing device 20 should be, for example, less than 20- or 10-times of the stroke volume. The ratio of the stroke volume and the dead volume may be referred to as the compression ratio of the micropump.

In case the microdosing device 20 comprises a tubing element 28 as the fluid sample outlet 22 for supplying the fluid sample 24 in an immediate proximity to the user's nose, the tubing element 28 should be as short as possible so that the volume of the tubing element 28 is for example less than 5- or 3-times the stroke volume.

The following evaluations relate to the so-called dead volume of the microdosing device 20. According to the present invention, the dead volume between the exit of the micropump 21 and the nose of the user should be as small as possible. Taking into account that the micropump 21 can deliver small quantities very accurately, e.g. with an exemplary stroke volume of 0.25 µl, the air volume containing the fluid sample molecules (e.g. the scent sample) should be transported immediately to the nose. The following estimation shows a possible dead volume of a microdosing device:

TABLE 1

|  | Length (mm) | Cross section (mm$^2$) | Dead volume [µl] |
| --- | --- | --- | --- |
| Dead volume inside the silicon pump chip | 0.5 | 5 | 2.5 |
| Dead volume inside the silicone gasket | 0.2 | 5 | 1.0 |
| Dead volume inside the outlet hole of the carrier | 5.0 | 0.5 | 2.5 |
| Dead volume of the tubing (ID* 0.2 mm) | 40 | 0.04 | 1.6 |
| Total Dead volume between pump and nare |  |  | 7.6 |

*inner diameter

As a result of the above dimensions of the dead volume and a total dead volume of about 7.6 µl, the microdosing device has to pump nearly 30 pump strokes, until the first scent appears to the nare of the user's nose. Therefore, when performing dispensing procedures, the dosing accuracy is not limited by the stroke volumes or the accuracy of the micropump 21, but by the total dead volume between the micropump 21 of the microdosing device 20 and the user's nare.

Thus, the following measures can be taken to reduce the total dead volume:

Grinding the bottom wafer for reducing the thickness (e.g. from 450 µl to 100 µl), Reducing the thickness of the gasket (e.g. to 50 µl), Reducing the length of the hole (e.g. to 1 mm), Reducing the length of the tubing element (e.g. to 20 mm)

Based on the above measures, the total dead volume can be drastically reduced. The following Table 2 shows exemplarily changed dimensions.

TABLE 2

|  | Length (mm) | Cross section (mm$^2$) | Dead volume [µl] |
| --- | --- | --- | --- |
| Dead volume inside the silicon pump chip | 0.1 | 5 | 0.5 |
| Dead volume inside the silicone gasket | 0.05 | 5 | 0.25 |
| Dead volume inside the outlet hole of the carrier | 1.0 | 0.5 | 0.5 |
| Dead volume of the tubing (ID* 0.1 mm) | 40 | 0.01 | 0.4 |
| Total Dead volume between pump and nare |  |  | 1.65 |

*inner diameter

Thus, only seven pump strokes are needed to pump the scent sample to the users's nare. A further alternative arrangement is to arrange the outlet of the silicon chip directly in front of the user's nare. However, the fixing element or the headset as part of the fixing element have to be accordingly redesigned. Moreover, arranging the outlet of the silicon chip, i.e. the micropump 21, together with a nozzle directly bonded to the silicon chip, directly in front of the nare allows to dose every pump stroke without any dead volume.

The microdosing driver unit 30 is, for example, configured to activate the microdosing device 20 responsive to a control signal as a control received from a computer, video game consol (e.g. an interactive entertainment computer), or any platform or device (e.g. a smart phone, DVD player, Blu-ray player etc.) for playing audio-visual media including books, periodicals, movies, music, games and web content. The microdosing driver unit 30 may comprise a wireless receiver 34 for installing a wireless connection to the remote system controller (not shown in FIG. 1a). Alternatively, the microdosing driver unit 30 of the sample dispenser 10 may be connected to the remote system control by means of a signal line integrated into a connection cable which may be electrically and mechanically coupled to a headset. Moreover, the remote controllable scent sample dispenser 10 may comprise a power supply element 70, for example in the form of a replaceable battery or a rechargeable battery. The power supply element in the form of the battery 70 may be integrated into the microdosing driver unit 30, the microdosing device 20 or the fixing element 40 and may be electrically coupled to the microdosing device 20 and/or the microdosing driver unit 30.

Alternatively, the necessitated power for energizing the microdosing device 20 and the microdosing driver unit 30 may be supplied over a power supply line which may be integrated into a connection cable to a headset within which the fluid sample dispenser 10 may be integrated.

As the fluid sample dispenser 10 may be integrated into headset equipment, the fluid dispenser 10 may be applied to be used with a telephone headset, a computer headset, a mobile phone headset, a wireless headset, a DECT wireless headset, a 2.4 GHz wireless headset or a Bluetooth wireless headset, for example.

As shown in FIG. 1a, the fluid sample reservoir 60 is arranged (with respect to the intended flow direction of the fluid sample) upstream to the microdosing device 20 having the micropump 21, so that the microdosing device 20 sucks the fluid sample 24 from the fluid sample reservoir 60 and through connecting tubing elements and supplies the precisely dosed fluid sample 24 at the fluid sample outlet 22 to the environment.

Figure 1B:
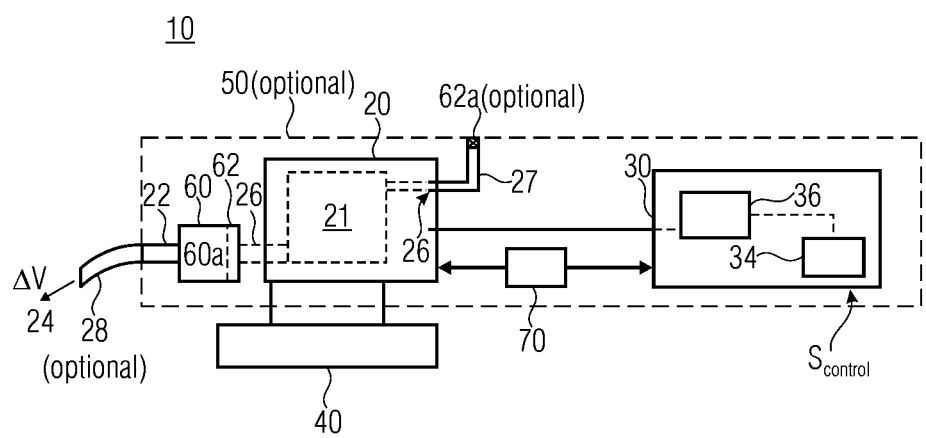

Alternatively, the fluid sample reservoir 60 may be arranged (with respect to the intended flow direction of the fluid sample 24) downstream to the microdosing device 20 as exemplarily illustrated in FIG. 1b so that the microdosing device 20 may supply the fluid sample 24 to the environment by pushing air or gas through the fluid sample reservoir 60 and then through the fluid sample outlet 22 to the environment.

As exemplary shown in FIG. 1b, the inlet 26 of the micropump 21 may be fluidically coupled, e.g. via an optional fluid channel 27 and a filter element 62a, to the environment. The optional filter element 62a may be an active carbon filter. The filter element 62a may filter out potential contaminations or other undesired substances from the environment and may also prevent molecules of the fluid sample 24 from leaking from the micropump 21 to the environment. The (optional) filter element 62 of the reservoir 60 may prevent molecules of the fluid sample 24 from leaking to the micropump 21.

The remaining functional elements of the fluid sample dispenser 10 of FIG. 1b can be implemented as described with respect to the fluid sample dispenser 10 of FIG. 1a.

Figure 1C:
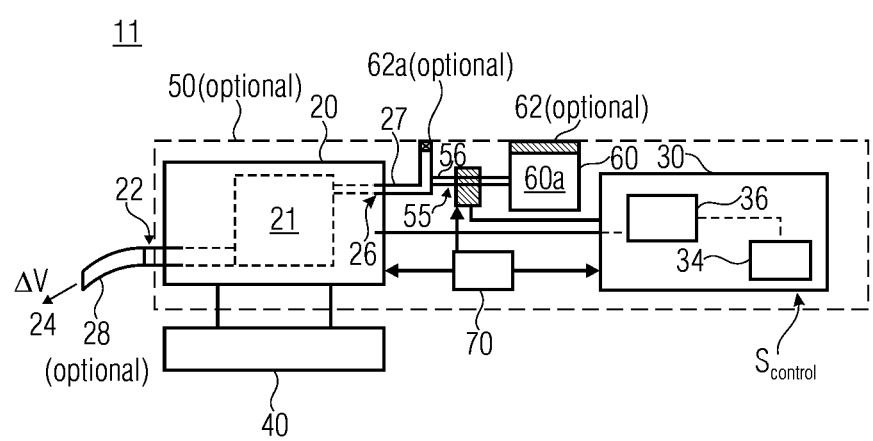

As exemplarily shown in FIG. 1c, the reservoir 60 is separately arranged to the flowing path of the carrier gas created by the microdosing device 20. To be more specific, the fluid sample dispenser 11 comprises the microdosing device 20 fluidically coupled to the fluid sample outlet 22, wherein the microdosing device 20 is configured to create, during an activation state, a flow of a carrier gas to the fluid sample outlet 22. The microdosing device 20 further comprises a fluid sample supply means 55 fluidically coupled to the fluid sample reservoir 60 having, for example, optionally the filter element 62 to the environment. As depicted in FIG. 1c, the fluid sample means 55 and the reservoir 60 may be connected at an upstream position with respect to the microdosing device 20. However, it should become clear that the fluid sample supply means 55 and the reservoir 60 may also be arranged at a downstream position with respect to the microdosing device 20. The fluid sample supply means 55 is configured to selectively supply particles of the fluid sample from the fluid sample reservoir 60 into the carrier gas flowing to the fluid sample outlet 22. The fluid sample dispenser 11 may further comprise a microdosing driver unit 30 for adjusting a dosing rate of the fluid sample 24 output at the fluid sample outlet 22 by selectively activating the microdosing device 20 and the fluid sample supply means 55, if the fluid sample supply means 55 is an active supply element. Moreover, the power supply element 70 of the remote controllable scent sample dispenser 10 may also be electrically coupled to the fluid sample supply means 55 for supplying the fluid sample supply means 55 with energy. Alternatively, the necessitated power for energizing the fluid sample supply means 55 may be supplied over a power supply line which may be integrated into a connection cable to a headset within which the fluid sample dispenser 11 may be integrated. The fluid sample supply means 55 may, for example, comprise a further micropump having a pump chamber providing a defined stroke volume $\Delta V_1$.

The remaining functional elements of the fluid sample dispenser 11 of FIG. 1c can be implemented as described with respect to the fluid sample dispenser 10 of FIG. 1a or 1b.

An alternative embodiment of the remote controllable fluid sample dispenser 11, as depicted using FIG. 1c, allows omitting a second micropump, wherein the fluid sample supply means 55 implements a mixer structure (not shown) which sucks in or injects the particles of the fluid sample 24 from the reservoir 60 into the stream of the carrier gas for forming the fluid sample 24 to be output. Thus, a small opening or small hole (not shown), e.g. at a bottlenecked section of the fluid channel, may be formed in the fluid channel in which the carrier gas flows, exemplarily in an upstream or a downstream position to the microdosing device 20, wherein the opening is configured to be of a size such as a small quantity (e.g. a predefined number of particles) of the fluid sample 24 stored in the reservoir 60 is injected into the flow (or gas stream) of the carrier gas with the suction stroke by the micropump of the microdosing device 20, i.e. when there is a negative pressure in the fluid channel 56 which forms the connection between the fluid channel 27 of the carrier gas and the reservoir 60. The opening 55 (i.e. the fluid sample supply means) is either selected to be so small that the particles of the fluid sample cannot escape from it, or a valve element, such as for example in form of a film covering the opening, may be used. As a further alternative, the fluid sample supply means 55 may be implemented as an opening at a bottleneck-shaped section (not shown) of the fluid channel 27 of the carrier gas.

With respect to the above embodiments as described with respect to FIGS. 1a-c, 2a-i and 3, the fluid sample outlet 22 may comprise a nozzle or a nozzle structure (not shown) for increasing the flow speed of the fluid sample 24 output at the fluid sample outlet 22 to the environment. The nozzle or nozzle structure may be integral to the fluid sample outlet 22 or may be a separate element securely fixed to the fluid sample outlet 22.

The nozzle or nozzle structure associated to the fluid sample outlet 22 may be any element decreasing the cross-sectional area of the fluid path at the fluid sample outlet 22. Thus, the nozzle or nozzle structure may be implemented by a bottleneck-shaped section of the fluid channel at the fluid sample outlet 22. The nozzle or nozzle structure may be a thin metal plate having an orifice (e.g. etched, or laser drilled), a small silicon chip with an KOH etched or dry etched orifice, a pipe or tube of varying cross-sectional area and it can be used to direct or modify the flow of the fluid sample 24 output at the fluid sample outlet 22 to the environment. Thus, such a nozzle or nozzle structure can be used to control the rate of flow, speed, direction, mass, shape and/or the pressure of the fluid sample stream that emerges therefrom. In order to avoid an unnecessitated increase of the dead volume of the inventive fluid sample dispenser 10/11, the nozzle or nozzle structure can be integrally incorporated into the fluid sample outlet 22 or the tubing element 28 (if present). Practically, the nozzle or nozzle structure at the fluid sample outlet may be a decrease of the cross-sectional area of the fluid channel by approximately 20 to 95% (or 40 to 60%). However, it should be ensured that the utilization of a nozzle or nozzle structure does not affect the functionality or efficiency of the microdosing device 20 when creating the flow of the carrier gas. Thus, the chosen nozzle type may depend on the design of the respectively used micropump.

Another embodiment to adapt the nozzle to the microdosing element like a silicon or metal micropump is to adapt the nozzle chip directly to the outlet of the silicon chip, that means that the nozzle is adapted at the bottom side of the micropump chip (e.g. by Silicon Fusion Bond, by gluing or by laser welding), and the pump chip is arranged in a way that the nozzle is directed to the user's nose. With that the dead volume between outlet valve of the pump and nozzle can be reduced to less than 0.2 µl (e.g. dry etched valve, size of the outlet valve hole e.g. 0.5×1.0×0.4 m$^3$=0.2 mm$^3$=0.2 µl). Another advantage of this embodiment is that not only the dead volume, but also the fluidic capacitances of the outlet 22 is very small due to the stiff materials (silicon, metal), with that very small amounts of fluid samples can be dispensed and changed very quickly.

Based on the increase of the flow velocity of the fluid sample outlet 22, greater distances from about 10 cm (e.g. 5 to 15 cm or 8 to 12 cm) between the fluid sample outlet 22 and the user's nose may be bridged. Thus, the inventive fluid sample dispenser 10/11 may be arranged in a greater distance from the user's nose so that a greater acceptance of the dispenser by the user may be achieved without any deterioration of the desired/adjusted dosing rate.

Moreover, it should be noted that all parts and functional elements of the fluid sample dispenser 10 as shown in FIGS. 1*a-c* and, also, the materials used therefore should be designed to avoid and suppress (as far as possible) any undesired leaking or diffusion of components of the fluid sample 24 to the environment.

Further designs and additional functional elements, which may be optionally added to the remote controllable fluid sample dispenser 10/11 illustrated in FIGS. 1*a-c* and the functionality thereof in cooperation with the functional elements described before, will be subsequently described referring to possible implementations as illustrated in FIGS. 2*a-i*.

To be more specific, subsequently alternative implementations of the inventive (remote controllable) fluid sample dispenser 10/11 in accordance with further embodiments will be discussed making reference to FIGS. 2*a-i*. With regard to the further description based on FIGS. 2*a-i*, it is pointed out that the elements of the controllable fluid sample dispenser 10/11, which are identical in their function and/or have the same function or the same effect as those elements of the fluid sample dispenser 10/11 illustrated in FIGS. 1*a-c*, are still provided with the same reference numbers. Thus, the description of these elements and the functionality thereof illustrated in the different embodiments is mutually exchangeable and may be applied to one another in the different embodiments.

Figure 2A:
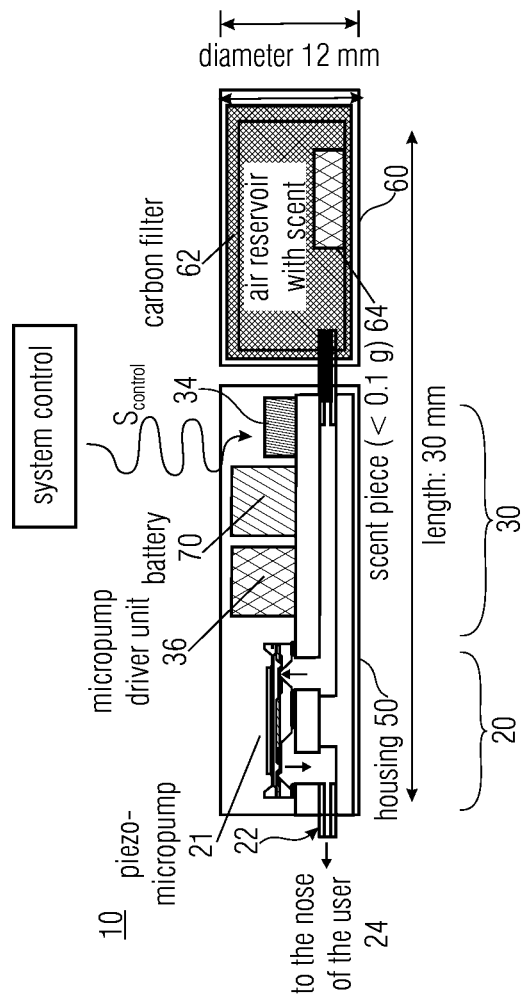

As depicted in FIG. 2*a*, the remote controllable fluid sample dispenser 10 exemplarily comprises the microdosing device 20 in form of a piezo-micropump 21 for outputting, during an activated condition, the fluid sample 24 at the scent sample outlet 22 to the environment. The microdosing driver unit 30, which is optionally integrated into a common housing 50 with the microdosing device 20 comprises the micropump driver unit 36, the battery 70 and the (e.g. wireless) control signal receiving element 34. Furthermore, a fluid sample reservoir 60 is fluidically coupled to the piezo-micropump 20. The reservoir 60 contains a piece 64 of a fluid sample creating material such as in the form of a scent, aroma, flavor, and/or medical or pharmaceutical agent. Moreover, the reservoir 60 comprises a filter element 62 which is pervious to gas of the environmental atmosphere, but avoids (as far as possible) leaking of the fluid sample 24 from the inner volume of the reservoir 60 to the environment.

As outlined in FIG. 2*a*, exemplary outer dimensions of the housing 50 of the remote controllable scent sample dispenser 10 are, for example, 30 mm in length and 12 mm in diameter.

As outlined in FIG. 2*a*, the reservoir comprises a scent piece (e.g. smaller than 0.1 g) as the scent creating material 64, wherein scent molecules of the scent material are dissolved in air, and during activation of the microdosing device 20 in form of a piezo-micropump 21, are supplied to the scent sample outlet 22. In this context, it is to be kept in mind that the fluid sample creating material 64 arranged in the inner volume of the reservoir 60 may be any material on the field of scent, aroma, flavor or medical/pharmaceutical applications, which a person/user may sense, smell or may be applied to for medical, wellness or entertainment applications.

As shown in FIG. 2*a*, the scent sample reservoir 60 is arranged upstream to the microdosing device 20 having the micropump 21, so that the microdosing device 20 sucks the fluid sample from the fluid sample reservoir 60 through connecting tubing elements and supplies the precisely dosed fluid sample at the scent outlet 22 to the environment.

Figure 2B:
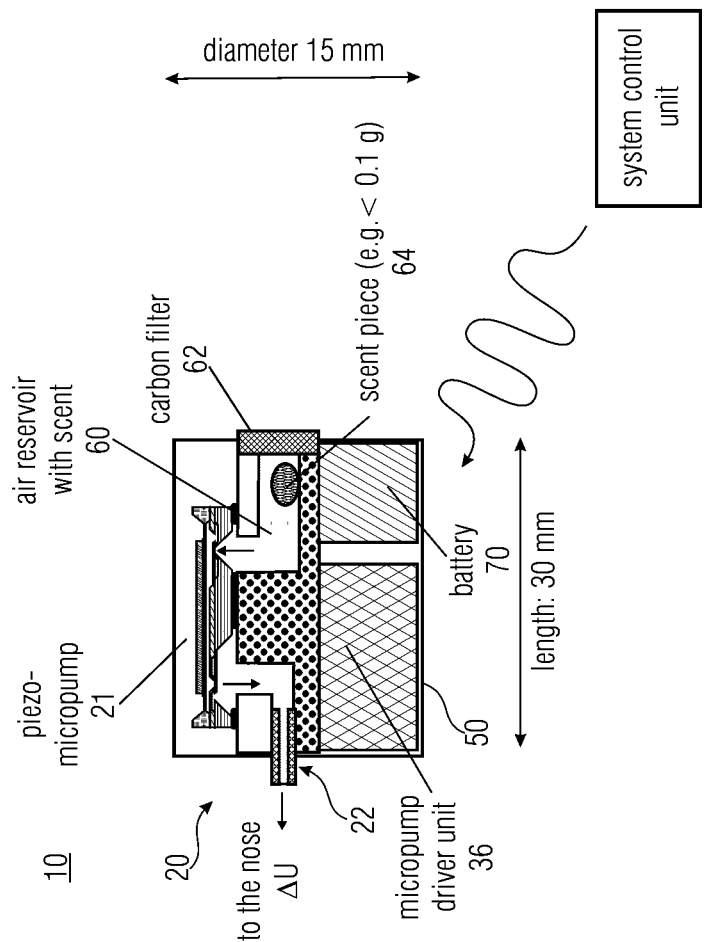

As depicted in FIG. 2*b*, the remote controllable fluid sample dispenser 10 exemplarily comprises the microdosing device 20 in the form of a piezo-micropump 21 for outputting, during an activated condition, the fluid sample 24 at the fluid sample outlet 22 to the environment. The microdosing driver unit 30 which is integrated into a common housing 50 with the microdosing device 20 comprises the micropump driver unit 36, the battery 70 and a (e.g. wireless) control signal receiving element (not shown). Furthermore, the scent sample reservoir 60 is fluidically coupled to the inlet of the piezo-micropump 20. The reservoir 60 is implemented as a fluid channel connected to the inlet 26 of the piezo-micropump 20 and separated by means of the filter element 62 from the environment, wherein the fluidic channel comprises, for example, a piece of a fluid sample creating material 64 so that the fluid sample molecules are dissolved in a gas, for example air, provided through the filter element 62 from the environment. The fluid sample molecules dissolved in the gas form the fluid sample 24 and are provided to the fluid sample outlet 22 by means of the activated piezo-micropump 21. The fluid channels, which form the inlet 26 and outlet 22 of the microdosing device 20 may be formed as capillaries or micro-capillaries.

The reservoir 60 comprises a filter element 62 which is pervious to gas of the environmental atmosphere, but avoids (as far as possible) leaking of the fluid sample 24 from the reservoir 60 to the environment. As outlined in FIG. 2*b*, exemplary outer dimensions of the housing 50 of the remote controllable fluid sample dispenser 10 are, for example, 15 mm in diameter and 30 mm in length.

With respect to the following description of the embodiments as illustrated in FIGS. 2*c-i*, it is pointed out to the fact that only different configurations of the fluid sample reservoir 60 fluidically coupled to the micropump 21 are illustrated, wherein the above description of the (optionally) additional functional elements, such as the microdosing driver unit 30, the micropump driver unit 36, the battery 70, the control signal receiving element 34, the housing 50, the fixing element 40 etc. is equally applicable to the following exemplary embodiments.

Figure 2C:
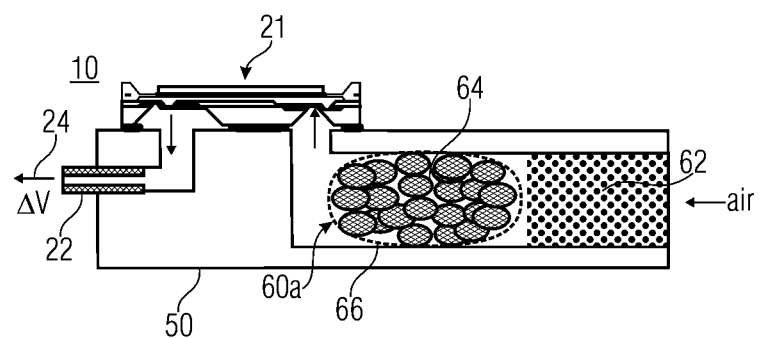

As depicted in FIG. 2*c*, the remote controllable fluid sample dispenser 10 exemplarily comprises the microdosing device 20 in form of a piezo-micropump 21 or a micro-fan for outputting, during an activated condition, the fluid sample 24 at the fluid sample outlet 22 to the environment. Furthermore, a fluid sample reservoir 60 is fluidically coupled to the piezo-micropump 20. To be more specific, the reservoir 60 is implemented as fluid channel fluidically coupled to the inlet 26 of the piezo micropump 21 and is separated by means of a filter element 62 from the environment, wherein the fluid channel comprises, for example, a piece of a fluid sample creating material 64 so that the fluid sample molecules are dissolved in gas, for example air, provided through the filter element 62 from the environment. The filter element 62 is pervious to gas of the environmental atmosphere and avoids (as far as possible)

leaking of the fluid sample 24 from the inner volume of the reservoir 60 to the environment.

As shown in FIG. 2c, the piece(s) of the fluid sample creating material 64 are arranged within a bag 66 (e.g. a filter bag) which facilitates refilling the reservoir 60 with a new bag filled with new piece(s) of the fluid sample creating material 64.

In order to exchange the bag with the pieces of the fluid sample creating material 64, the filter element 62 may be removed for getting access to the inner volume 60a of the fluid sample reservoir 60. After replacing the bag 66 by a new bag having the new piece(s) of the fluid sample creating material 64, the filter element 62 is again installed to the reservoir 60. Optionally, a new filter element 62 may be installed, in case the carbon material of the filter element 62 is already saturated by the scent sample molecules.

Figure 2D:
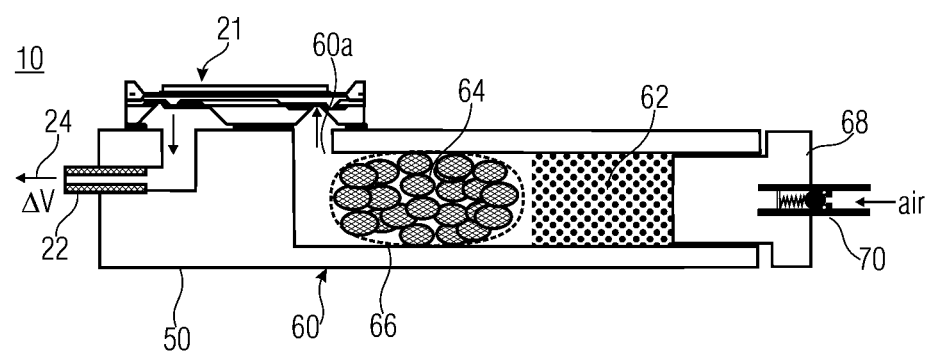

As it is depicted in FIG. 2d, the fluid sample dispenser 10 comprises in addition to the remote controllable fluid sample dispenser 10 of FIG. 2c, a fluid channel cap or cover 68 and a free flow protection element 70, e.g. in form of a (threshold) check valve, for preventing, during an inactivated (non-operated) state of the micropump 21, an undesired flow of the fluid sample 24 in a flow direction opposite to the intended flow direction of the fluid sample 24 to the outlet 22 of the piezo-micropump 21. The fluid channel cap or cover 68 may be replaceably positioned in a upstream position to the filter element 62 for sealing the fluid channel. In an activated state of the micropump 21, environmental air can pass the free flow protection element 70 and the filter element 62, in order to be provided to the inner volume 60a of the reservoir 60. The fluid channel cap or cover 68 and the filter element 62 may be removed for getting access to the inner volume 60a of the fluid sample reservoir 60, in order to exchange the fluid sample creating material 64 with a new fluid sample creating material within the reservoir 60.

Figure 2E:
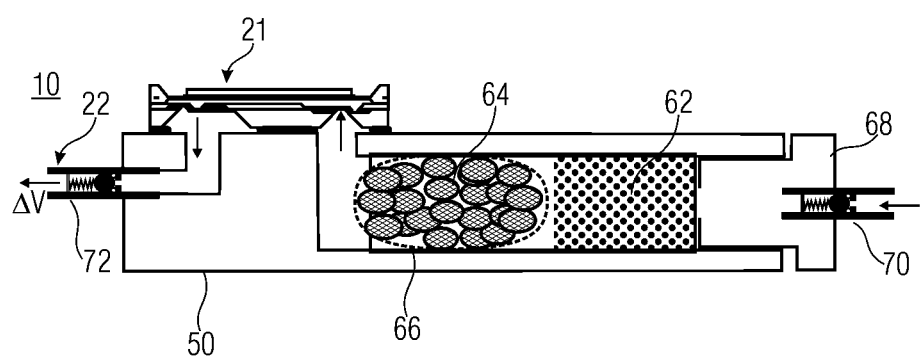

As it is depicted in FIG. 2e, the fluid sample dispenser 10 comprises in addition to the remote controllable fluid sample dispenser 10 of FIG. 2d, a further free flow protection element 72, e.g. in form of a check valve, at the outlet 22 of the piezo-micropump 21, for preventing, during an inactivated (non-operated) state of the micropump 21, an undesired flow of the fluid sample in a flow direction opposite to the intended flow direction of the fluid sample 24 which is from the pump chamber to the outlet 22 of the piezo-micropump 21.

Figure 2F:
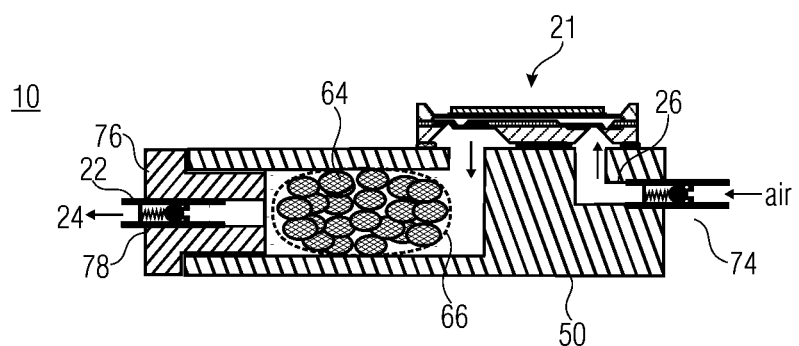

As it is depicted in FIG. 2f, the remote controllable fluid sample dispenser 10 exemplarily comprises the microdosing device 20 in form of a piezo-micropump 21 for outputting, during an activated condition, the fluid sample 24 at the fluid sample outlet 22 to the environment. Furthermore, a fluid sample reservoir 60 is fluidically coupled at a downstream position to the piezo-micropump 21. To be more specific, the reservoir 60 is implemented as fluid channel fluidically coupled to the outlet 22a of the piezo-micropump 21 and is separated by means of a free flow protection element 78 from the environment, wherein the fluid channel comprises, for example, a piece 64 of a fluid sample creating material so that the fluid sample molecules are dissolved in gas, for example air, provided through the piezo-micropump 21 from the environment.

The free flow protection element 78, e.g. in form of a check valve, is formed in a fluid channel cap or cover 76 and prevents, during an inactivated (non-operated) state of the micropump 21, an undesired flow of the fluid sample 24. The fluid channel cap or cover 76 may be replaceably positioned in a downstream position to the piezo-micropump 21. The fluid channel cap or cover 76 and the filter element 62 may be removed for getting access to the inner volume 60a of the fluid sample reservoir 60, in order to replace the bag 66 with the fluid sample creating material 64 by a new fluid sample creating material within the reservoir 60.

With respect to the above embodiments of FIGS. 2c-f, it is pointed out to the fact that the microdosing device 20 and the reservoir 60 can be formed in a common substrate. Thus, the fluid sample dispenser 10 can realize a scent dosing system with a very tightly closed housing 50.

Figure 2G:
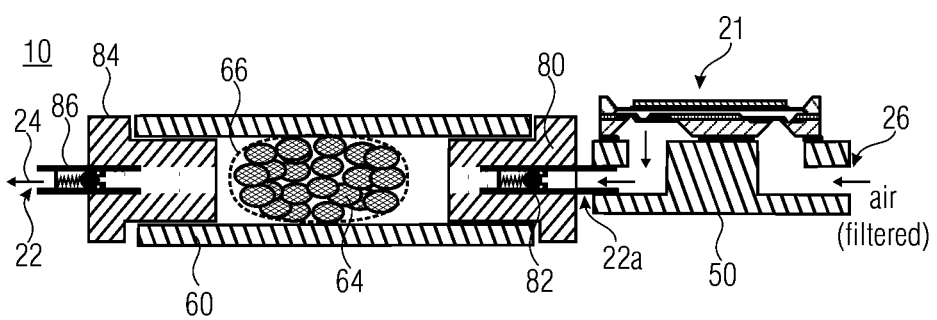

As it is depicted in FIG. 2g, the fluid sample dispenser 10 exemplarily comprises the microdosing device 20 in form of a piezo-micropump 21 for outputting, during an activated condition, the fluid sample 24 at the fluid sample outlet 22 to the environment. Furthermore, a fluid sample reservoir 60 is fluidically coupled to the piezo-micropump 20. To be more specific, the reservoir 60 is implemented as fluid channel fluidically coupled to the outlet 22a of the piezo-micropump 21, i.e. is positioned downstream to the piezo-micropump 21, wherein the fluid channel 60 (e.g. in form of a glass or plastic tubing element) comprises, for example, a piece 64 of a fluid sample creating material so that the fluid sample molecules are dissolved in gas, for example air, provided through the piezo-micropump 21 from the environment. A filter element (not shown), which is pervious to gas of the environmental atmosphere and avoids (as far as possible) leaking of the fluid sample 24 from the piezo-micropump 21 to the environment, my be positioned upstream to the fluid inlet 26 of the piezo-micropump 21.

The reservoir 60 formed by a fluid channel downstream to the micropump 21 comprises a first fluid channel cap or cover 80 with a first free flow protection element 82 and a second fluid channel cap or cover 84 with a second free flow protection element 86. The first and second fluid channel caps 80, 84 with the first and second free flow protection elements 82, 86 are positioned at the two opposing openings (access or connections ports) of the reservoir 60. Thus, the reservoir 60 can be reliably sealed during an inactivated (non-operated) state of the micropump 21. Thus, the reservoir 60 can be easily removed from or attached to the microdosing device 20 without any risk of leaking. The reservoir 60 can be implemented as disposable (one-way) fluid sample container or cartridge.

As it is depicted in FIG. 2h, the fluid sample dispenser 10 again exemplarily comprises the microdosing device 20 in form of a piezo-micropump 21 for outputting, during an activated condition, the fluid sample 24 at the fluid sample outlet 22 to the environment. Furthermore, a fluid sample reservoir 60 is fluidically coupled to the piezo-micropump 20, i.e. is positioned upstream to the piezo-micropump 21. To be more specific, the reservoir 60 is implemented as fluid channel fluidically coupled to the inlet of the piezo micropump 21 and is separated by means of a first fluid channel cap or cover 80 with a first free flow protection element 82 from the environmental atmosphere (gas or air), wherein the fluid channel comprises, for example, in a bag 66 a piece 64 of a fluid sample creating material so that the fluid sample molecules are dissolved in a gas provided through first free flow protection element 82 from the environment.

The reservoir 60 formed by a fluid channel upstream to the micropump 21 comprises the first fluid channel cap or cover 80 with the first free flow protection element 82 and a second fluid channel cap or cover 84 with a second free flow protection element 86. The second fluid channel cap or cover 84 with the second free flow protection element 86 are fluidically coupled to the inlet 26 of the micropump 21. The first and second fluid channel caps 80, 84 with the first and second free flow protection elements 82, 86 are positioned at the two opposing openings (access or connections ports) of the reservoir 60. Thus, the reservoir 60 can be reliably sealed during an inactivated (non-operated) state of the micropump 21. The reservoir 60 can be easily removed from or attached to the microdosing device 20 without any risk of leaking. The reservoir 60 can be implemented as disposable (one-way) fluid sample container or cartridge. The fluid sample reservoir 60 in form of fluid channel may comprise a glass or plastic tubing element.

As it is depicted in FIG. 2i, the fluid sample dispenser 10 again exemplarily comprises the microdosing device 20 in form of a piezo-micropump 21 for outputting, during an activated condition, the fluid sample 24 at the fluid sample outlet 22 to the environment. Furthermore, a fluid sample reservoir 60 is fluidically coupled to the piezo-micropump 20. To be more specific, the reservoir 60 is implemented as fluid channel fluidically coupled to the inlet 26 of the piezo micropump 21 and is separated by means of a first fluid channel cap or cover 80 with a first free flow protection element 82 from the environmental atmosphere (gas or air), wherein the fluid channel comprises, for example, in a bag 66 a piece 64 of a fluid sample creating material so that the fluid sample molecules are dissolved in gas, for example air, provided through first free flow protection element 82 from the environment.

As a difference to the arrangement of FIG. 2h, the micropump 21 of FIG. 2i comprises a second free flow protection element 86 at the outlet 22 instead of the second fluid channel cap or cover 84 with the second free flow protection element 86 at the outlet of the reservoir 60. Thus, in a connected configuration, the micropump 21 and the reservoir 60 can be reliably sealed during an inactivated (non-operated) state of the micropump 21. Moreover, the reservoir 60 may comprise a septum (not shown), which may be pierced by the inlet 26 of the micropump 21 when fluidically connecting the micropump 21 to the fluid sample reservoir 60. Thus, the reservoir 60 can be easily removed from or attached to the microdosing device 20 without any risk of leaking. The reservoir 60 can be implemented as disposable (one-way) fluid sample container or cartridge. The fluid sample reservoir 60 in form of fluid channel may comprise a glass or plastic tubing element.

With respect to the above embodiments of FIGS. 2a-i, it is pointed out to the fact that the respective free flow protection elements may comprise a threshold check valve, for preventing as far as possible, during an inactivated (non-operated) state of the micropump 21, an undesired leaking of the fluid sample 24 out of the piezo-micropump 21 and/or an access of a environmental gas to the interior of the micropump 21 or the fluid sample reservoir 60 (i.e. the fluid path). Moreover, the threshold (fluid flow resistance) of the respective free flow protection elements is adjusted so that, during an activated or operated state of the micropump 21, the respective free flow protection elements provide an one-way fluid path for the fluid sample 24 to be supplied at the outlet 22 of the microdosing device 20 to the environment. The one-way fluid path extends through the reservoir 60 and the fluidically connected micropump 21 and is enabled by means of the fluid pressure generated by the activated micropump 21.

Figure 3:
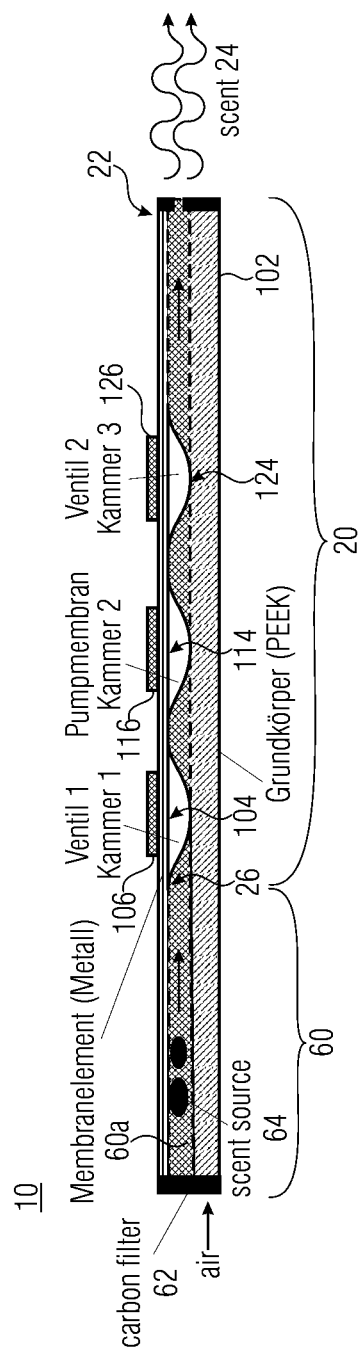
FIG. 3 shows a schematic illustration of an exemplary implementation of the microfluidic dosing system in form of a peristaltic pump in accordance with another embodiment of the present invention.

FIG. 3 shows a peristaltic micropump 10 on a base body 102, each having a first membrane region 104 with a first piezo-actuator 106 for actuating the first membrane region 104, a second membrane region 114 with a second piezo-actuator 116 for actuating the second membrane region 114, a third membrane region 124 with a third piezo-actuator 126 for actuating the third membrane region 124.

As depicted in FIG. 3, the remote controllable fluid sample dispenser 10 exemplarily comprises the microdosing device 20 in form of a piezo-micropump 21 or a micro-fan for outputting, during an activated condition, the fluid sample 24 at the fluid sample outlet 22 to the environment. Furthermore, a fluid sample reservoir 60 is fluidically coupled to the piezo-micropump 20. To be more specific, the reservoir 60 is implemented as fluid channel fluidically coupled to the inlet 26 of the piezo micropump 21 and is separated by means of a filter element 62 from the environment, wherein the fluid channel comprises, for example, a piece of a fluid sample creating material 64 so that the fluid sample molecules are dissolved in gas, for example air, provided through the filter element 62 from the environment. The filter element 62 is pervious to gas of the environmental atmosphere and avoids (as far as possible) leaking of the fluid sample 24 from the inner volume 60a of the reservoir 60 to the environment.

For the peristaltic micropump 10 the pump body 102 forms, together with the first membrane region 104, a first valve (chamber 1) whose passage opening is open in the non-actuated state of the first membrane region 104 and whose passage opening may be closed by actuating the first membrane region 104. The pump body 102 forms, together with the second membrane region 114, a pumping chamber (chamber 2) whose volume may be decreased by actuating the second membrane region 114. The pump body 102 forms, together with the third membrane region 124, a second valve (chamber 3) whose passage opening is open in the non-actuated state of the third membrane region and whose passage opening may be closed by actuating the third membrane region 124, wherein the first and second valves are fluidically connected to the pumping chamber.

At the peristaltic micropump 10, the first and second valves are open in the non-actuated state, wherein the first and second valves may be closed by moving the membrane towards the pump/base body, whereas the volume of the respective pumping chamber may be decreased by moving the respective second membrane region also towards the pump body 102. Thus, the peristaltic micropump 10 is normally open, so that (optionally) a safety valve or a different free-flow stop (not shown in FIG. 3) can be integrated.

Through this construction, the peristaltic micropump enables the realization of bubble-tolerant, self-priming pumps, even if piezo-elements arranged on the membrane are used as piezo-actuator.

In order to ensure that the peristaltic micropump 10 can work in a bubble-tolerant and self-priming manner, it is dimensioned such that the ratio of stroke volume and dead volume is greater than the ratio of delivery pressure (feed pressure) and atmospheric pressure, wherein the stroke volume is the volume displaceable by the pumping membrane, the dead volume is the volume remaining between inlet opening and outlet opening of the micropump, when the pumping membrane is actuated and one of the valves is closed and one is open, the atmospheric pressure is a maximum of about 1050 hPa (worst case consideration), and the delivery pressure is the pressure necessitated in the fluid chamber region of the micropump, i.e. in the pressure chamber, to move a first/second fluid (liquid/gas) interface past a place representing a flow constriction (bottleneck) in the microperistaltic pump, i.e. between the pumping chamber and the passage opening of the first or the second valve, including this passage opening.

If the ratio of stroke volume and dead volume, which may be referred to as compression ratio, satisfies the above condition, it is ensured that the peristaltic micropump works in a bubble-tolerant and self-priming manner.

A further increase of the compression ratio of the peristaltic micropump 10 may be achieved by adapting the contour of a pumping chamber structured in the pump body to the bend line of the pumping membrane, i.e. the bend contour thereof in the actuated state, so that the pumping membrane may substantially displace the entire volume of the pumping chamber in the actuated state. Furthermore, the contours of valve chambers formed in the pump body may also be correspondingly adapted to the bend line of the respective opposing membrane sections, so that in the optimum case the actuated membrane region substantially displaces the entire valve chamber volume in the closed state.

As shown in FIG. 3, an injection-molded part or injection-embossed part or powder injection moulded metal part can be used which has the peristaltic pumps realized on one side thereof. The membrane element can be joined by laser welding or other bonding technologies. The overall design of the scent dosing system of FIG. 3 is very cost efficient and can be used for mass production.

In the following, the principle functionality of the remote controllable fluid sample dispenser 10 and the inventive utilization of the described fluid sample dispenser 10 as well as the inventive (medical or clinical) testing procedures based on the inventive fluid sample dispenser 10 are described in detail.

To be more specific, the inventive remote controllable fluid sample dispenser 10 can be utilized for selectively supplying a fluid sample 24 with a predefined dosing rate to a person's nose. This precise fluid sample supply to a person's nose allows a medical examiner to test the person's scent detection sensitivity in a very efficient way. Thus, based on the defined distance between the outlet of the microdosing device and the test person's nose, and also on the very precise dosing rate, very expressive and comparable testing conditions can be achieved for testing and for comparing the minimum detection concentration of the person to be tested, for example at a clinical (medical) application.

Thus, the inventive remote controllable fluid sample dispenser 10 can be used to measure the lowest possible sensitivity of a test person to smell or taste a scent, flavor, aroma or fragrance etc., mainly by bringing very precise dosing rates of the fluid sample 24 from the fluid reservoir 60 to the person's nose by a microdosing device 20, e.g. in form of a micropump 21. The microdosing device 20 may be remote controlled over the microdosing driver unit 30, wherein the microdosing device 20 and, for example, the microdosing driver unit 30 may be fixed together adjacent to the person's nose so that a distance between an outlet 22 of a microdosing device and a nare of the person's nose is within a predefined range, e.g. less then 2 cm. Alternatively, only the microdosing device 20 is placed adjacent to the person's nose.

The fixing element 40 for fixing at least the microdosing device 20 and, optionally, the microdosing driver unit 30 adjacent to the person's nose may be implemented as a part of a headset fixed to the person's head. Thus, during an activation of the microdosing device 20, the fluid sample 24, e.g. in form of scent molecules dissolved in air, can selectively be supplied with a very precise, predefined dosing rate to the person's nose. In order to activate the remote controllable fluid sample dispenser 10, the medical examiner may activate the remote system controller, for example by pushing a button, wherein the control signal $S_{control}$ is transmitted to the microdosing driver unit by means of a wireless signal or by means of a line-coupled signal over a signal line. Due to the activation signal, the microdosing device outputs with a precise dosing rate the scent sample to the environment next to the person's nose.

As the stroke volumes $\Delta V$ of micropumps may be adjusted based on the electrical excitation, the remote system controller of the medical examiner may be equipped with different leveling means for adjusting the dosing rate (quantity per time unit) of the scent/fluid sample supplied to the test person's nose. Moreover, the time intervals for activating the microdosing device 20 may be adjusted over the remote system controller or a software routine implemented therein. To be more specific, the remote system controller may be equipped with a computer software for executing different testing routines which can be adapted to different testing concepts adapted for different groups or categories of test persons, for example differentiated by age, sex, symptoms, etc of the test persons to be examined.

During activation, the micropump of the microdosing device 21 supplies the scent sample 24 from the reservoir to the person's nose, wherein the scent sample comprises the scent molecules dissolved in air. As shown in FIG. 2a-i, the overall size of the remote controllable scent sample dispenser 10, comprising for example a micropump, a carrier substrate, the reservoir chamber, a carbon filter, may be implemented with very small dimensions, and advantageously with a volume of less than two cubic centimeters. In order to keep the dimensions of the scent sample dispenser 10 low, the air reservoir 60 is located next to the microdosing device 20 or is integrated to the microdosing device 20. Moreover, in order to prevent leaks and unnecessitated dead volumes, a tubing element 28 (see e.g. FIGS. 1a-c) at the scent sample outlet 22 of the microdosing device 20 should be kept short for providing a low tubing volume.

Figure 4A:
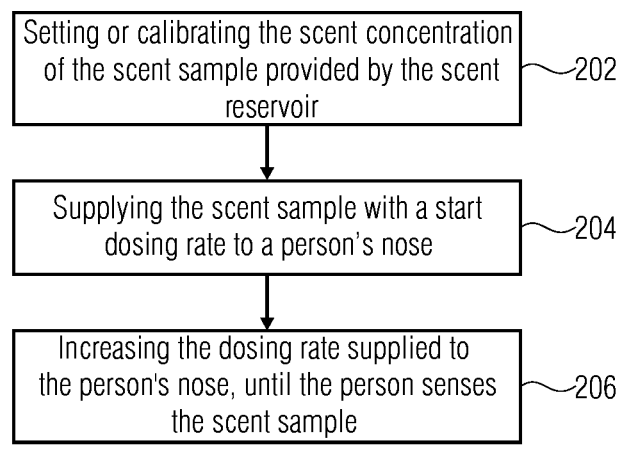
FIG. 4a-b shows a flowchart of a method for determining the minimum fluid sample concentration of a fluid sample a person can detect in accordance with another embodiment of the present invention.

A method 200 for determining the minimum scent concentration of a scent sample a person can detect, for example in the context of a clinical examination, in accordance with the present invention shall now be described below with reference to FIG. 4a. To be more specific, the inventive remote controllable scent sample dispenser 10 can also be used to measure the lowest detection concentration of a scent sample, for example in a scale of parts per million (ppm) or parts per thousand (ppt), that a test person can detect. In this connection, it is pointed out to the fact that a detection concentration of 1 ppm means that a person can detect one scent molecule in one million air molecules.

For example, a person can be tested with the inventive scent sample dispenser by releasing/supplying the scent sample to the person's nare by using the remote system controller of the medical examiner. First, the scent concentration of the scent sample in the scent reservoir is adjusted or calibrated 202. Then, the scent sample is supplied 204 to the person's nare with a start dosing rate, for example 1 ppm or 1 ppt. The start dosing rate is, for example, lower than the minimum dosing rate (minimum scent sample dose) the person to be tested can usually detect. The dosing rate supplied to the person's nare is (e.g. continuously or stepwise) increased 206, until the person senses or responds to the scent sample. Thus, the minimum scent concentration detectable by the person corresponds to the currently supplied dosing rate, when the person starts to sense to the supplied scent sample. Thus, the lowest dosing rate will be the minimum detection concentration of the scent the person can detect.

If the person (scent detection means) already responds to the scent sample supplied with the start dosing rate, the first dosing rate is reduced by at least 50% (or 90%) to a new start dosing rate, and the steps of supplying and increasing is performed by starting with the new start dosing rate.

Figure 4B:
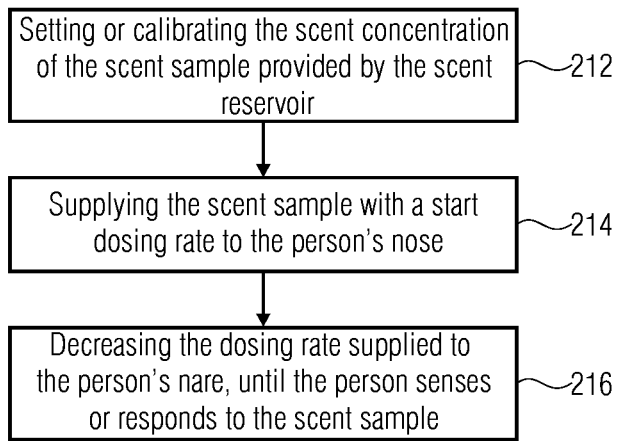

A method 210 for determining (a scent concentration of) a scent sample detection limit of a person in accordance with the present invention shall now be described below with reference to FIG. 4b. To be more specific, the inventive remote controllable scent sample dispenser 10 can also be used to measure the lowest detection concentration of a scent sample, for example in a scale of parts per million (ppm) or parts per thousand (ppt), that a person can detect.

For example, a person can be tested with the inventive scent sample dispenser by releasing/supplying the scent sample to the person's nare by using the remote system controller of the medical examiner. First, the scent concentration of the scent sample in the scent reservoir is adjusted or calibrated 212. Then, the scent sample is supplied 214 to the person's nare with a start dosing rate, for example 1 ppm or 1 ppt. The start dosing rate is, for example, higher than the minimum dosing rate (minimum scent sample dose) the person to be tested can usually sense. The dosing rate supplied to the person's nare is (e.g. continuously or stepwise) decreased 216, until the person stops to sense or respond to the scent sample, i.e. the person does not sense the scent sample any more. Thus, the scent sample detection limit of the person or the minimum scent sample concentration detectable by the person corresponds to the currently supplied dosing rate, when the person stops to sense the supplied scent sample.

If the person does not sense the scent sample supplied with the start dosing rate, the first dosing rate is increased by at least 50% (or 100%) to a new start dosing rate, and the steps of supplying and decreasing is performed by starting with the new start dosing rate.

In this connection, it is pointed to the fact the inventive remote controllable scent sample dispenser 10 can also be used to measure the lowest detection concentration of a scent sample, for example in a scale of parts per billion (ppb), parts per million (ppm), or parts per thousand (ppt), that a scent detection means can detect.

A method 300 for determining the minimum scent concentration of a scent sample, a scent detection means can detect, in accordance with the present invention shall now be described below with reference to FIG. 5a.

Figure 5A:
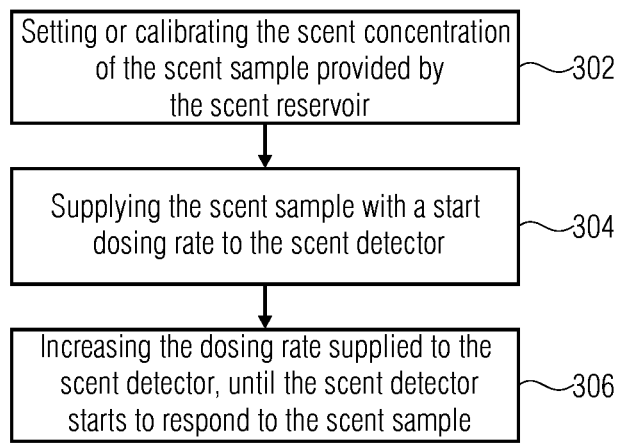
FIGS. 5a-b show flowcharts of methods for determining the minimum fluid sample concentration of a fluid sample, a fluid sample sensor can detect in accordance with another embodiment of the present invention.

In general, the inventive remote controllable scent sample dispenser 10 can be advantageously used for determining 300 the minimum scent concentration of a scent sample, a scent detection means can detect as shown in FIG. 5a. Thus, minute concentrations of scent samples can be supplied with a very high reliability in immediate proximity to a scent sensing element (sensor) of the scent detection means. To be more specific, the scent concentration of the scent sample provided by the scent reservoir, is adjusted or calibrated 302. The start dosing rate is, for example, lower than the minimum dosing rate (scent sample dose) the scent detection means to be tested can usually detect. Than, the scent sample is supplied 304 with the start dosing rate to a sensing element of the scent detection means, wherein the dosing rate supplied to the sensing element is (e.g. continuously or stepwise) increased 306, until the scent detection means responds to the scent sample. The minimum scent concentration detectable by the scent detection means corresponds to the currently supplied dosing rate, when the scent detection means responds to the supplied scent sample.

If the scent detection means already responds to the scent sample supplied with the start dosing rate, the first dosing rate by at least 50% (or 100%) is reduced to a new start dosing rate, and the steps of supplying and increasing is performed by starting with the new start dosing rate.

A method 310 for determining (a scent concentration of) the scent sample detection limit of a scent detection means in accordance with the present invention shall now be described below with reference to FIG. 5b.

Figure 5B:
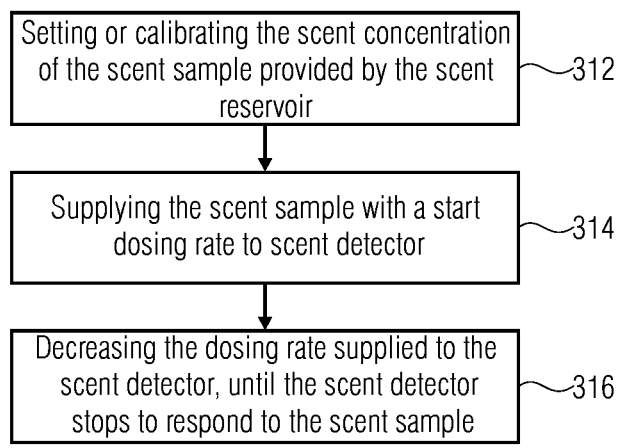

In general, the inventive remote controllable scent sample dispenser 10 can be advantageously used for determining 310 the scent sample detection limit of a scent detection means as shown in FIG. 5b. Thus, precisely dosed concentrations of scent samples can be supplied with a very high reliability in immediate proximity to a scent sensing element (sensor) of the scent detection means. To be more specific, the scent concentration of the scent sample provided by the scent reservoir, is adjusted or calibrated 312. The start dosing rate is, for example, higher than the minimum dosing rate (minimum scent sample dose) the scent detection means to be tested can usually detect. Than, the scent sample is supplied 314 with the start dosing rate to a sensing element of the scent detection means, wherein the dosing rate supplied to the sensing element is (e.g. continuously or stepwise) decreased 316, until the scent detection means stops to respond or detect to the scent sample, i.e. the scent detection means does not respond to the scent sample any more. Thus, the scent sample detection limit of the scent detection means or the minimum scent sample concentration detectable by the scent detection means corresponds to the currently supplied dosing rate, when the scent detection means stops to respond to or to detect the supplied scent sample.

If the scent detection means does not respond to the scent sample supplied with the start dosing rate, the first dosing rate by at least 50% (or 100%) is increased to a new start dosing rate, and the steps of supplying and decreasing is performed by starting with the new start dosing rate.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

Depending on certain implementation requirements, embodiments of the invention can be implemented in hardware or in software. The implementation can be performed using a digital storage medium, for example a floppy disk, a DVD, a Blue-Ray, a CD, a ROM, a PROM, an EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Generally, embodiments of the present invention can be implemented as a computer program product with a program code, the program code being operative for performing one of the methods when the computer program product runs on a computer. The program code may for example be stored on a machine readable carrier.

While this invention has been described in terms of several advantageous embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

The invention claimed is:

1. Fluid sample dispenser, comprising:
a microdosing device in form of a micropump that is fluidically coupled to a fluid sample reservoir and a fluid sample outlet for providing a one-way fluid path which extends through the reservoir and the fluidically coupled micropump and directly to the environment at the fluid sample outlet, the microdosing device being configured (1) to create, during an activation state of the micropump, a flow of a carrier gas from the environment, through the fluid sample reservoir for taking up fluid sample particles into the carrier gas and at the fluid sample outlet to the environment, and (2) to output a fluid sample in form of the carrier gas with the fluid sample particles at the fluid sample outlet to the environment, wherein the micropump comprises a pump chamber providing a stroke volume for creating, during the activation state of the micropump, the flow of the carrier gas through the fluid sample reservoir to the environment at the fluid sample outlet, and
a microdosing driver unit for adjusting a dosing rate of the fluid sample output to the environment at the fluid sample outlet by selectively activating the micropump.

2. Fluid sample dispenser according to claim 1, further comprising:
a fixing element for fixing and placing the microdosing device adjacent to the person's nose so that a distance between the fluid outlet of the microdosing device and a nostril of the person's nose is within a predefined range, or a tubing element at the fluid outlet of the microdosing device is placed at or in the nostril of the person's nose.

3. Fluid sample dispenser according to claim 1, wherein the microdosing driver unit is configured to activate the microdosing device responsive to a control signal received from a controller unit.

4. Fluid sample dispenser according to claim 1, wherein the fixing element is part of a headset attached to the person's head.

5. Fluid sample dispenser according to claim 1, wherein the microdosing driver unit comprises a signal receiving element for receiving the control signal from a controller unit remotely placed to the dispenser.

6. Fluid sample dispenser according to claim 5, wherein the signal receiving element is configured to install a wireless or wired connection through the controller unit.

7. Fluid sample dispenser according to claim 1, further comprising:
a power supply element in the form of a rechargeable battery.

8. Fluid sample dispenser according to claim 7, wherein the power supply element is integrated to the microdosing driver unit, the microdosing device or the fixing element.

9. Fluid sample dispenser according to claim 1, wherein the fluid sample reservoir is configured to provide the fluid sample with a specific sample concentration in form of fluid sample molecules or particles dissolved in filtered air from the environment.

10. Fluid sample dispenser according to claim 9, wherein the fluid sample comprises a scent, an aroma, flavor, and/or a medical or pharmaceutical agent.

11. Fluid sample dispenser according to claim 1, wherein the fluid sample reservoir is arranged, in the flow direction of the fluid sample, upstream to the microdosing device, wherein an inlet of the microdosing device is fluidically coupled to an outlet of the fluid sample reservoir.

12. Fluid sample dispenser according to claim 1, wherein the fluid sample reservoir is arranged, in the flow direction of the fluid sample, downstream to the microdosing device, wherein an outlet of the microdosing device is fluidically coupled to an inlet of the fluid sample reservoir.

13. Fluid sample dispenser according to claim 1, wherein the fluid sample reservoir is removably connected to the microdosing device.

14. Fluid sample dispenser according to claim 1, wherein the fluid sample reservoir is permanently attached to the microdosing device, wherein the microdosing device and the fluid sample reservoir are arranged in the same housing.

15. Fluid sample dispenser according claim 1, wherein the fluid sample reservoir comprises a plurality of separated volumes for storing different fluid samples.

16. Fluid sample dispenser according to claim 15, wherein the different fluid samples are selectively suppliable to the microdosing device.

17. Fluid sample dispenser according to claim 15, wherein the microdosing device comprises a plurality of micropumps, wherein the microdosing driver unit is configured to selectively or alternatively activate the plurality of micropumps, wherein each micropump is associated to a different volume of the plurality of separated volumes.

18. Fluid sample dispenser according to claim 15, further comprising a plurality of microdosing devices each fluidically coupled to one of the plurality of fluid sample volumes in the fluid sample reservoir.

19. Fluid sample dispenser according claim 1, wherein at least one of the inlet of the fluid sample reservoir, the outlet of the fluid sample reservoir, the inlet of the microdosing device and the outlet of the microdosing device comprise a free-flow protection element for preventing a fluid sample flow in a flow direction opposite to the intended fluid sample flow direction.

20. Fluid sample dispenser according to claim 1, wherein the microdosing device comprises a tubing element as the fluid sample outlet for supplying the fluid sample in immediate proximity to the nose or nostril of the person.

21. Fluid sample dispenser according to claim 1, wherein the microdosing device is configured to be placed adjacent to a person's nose so that a distance between the outlet of the microdosing device and a nostril of the person's nose is within a predefined range.

22. Fluid sample dispenser according to claim 1, wherein the fluid sample outlet comprises a nozzle or nozzle structure for increasing the flow speed of the fluid sample output at the fluid sample outlet to the environment.

23. Fluid sample dispenser according to claim 1, wherein the microdosing driver unit is configured to adjust the dosing rate of the fluid sample at the scent sample outlet to the environment based on the stroke volume of the micro pump and a number of pump strokes or diaphragm excursions for transporting a carrier gas in a predetermined direction to the fluid sample outlet.

24. Fluid sample dispenser according to claim 1, wherein the micropump comprises a peristaltic micropump.

25. Fluid sample dispenser according to claim 24, wherein a dead volume of the peristaltic micropump between an exit of the pump chamber and the outlet of the micropump is less than ten-times the stroke volume.

26. Fluid sample dispenser according to claim 1, wherein the ratio of stroke volume and dead volume is greater than the ratio of delivery pressure and atmospheric pressure, wherein the dead volume of the micropump is between an exit of the pump chamber and the outlet of the micropump.

27. Fluid sample dispenser according to claim 1, wherein the microdosing device is configured to create, during the activation state, the flow of the carrier gas from the environment of the dispenser into the fluid sample reservoir, through the fluid sample reservoir for taking up the fluid sample particles into the carrier gas, and at the fluid sample outlet to the environment.

28. Fluid sample dispenser according to claim 27, wherein the microdosing device is configured to create, during the activation state, the flow of the carrier gas from the environment of the dispenser through a filter element into the fluid sample reservoir.

29. Method of selectively supplying a fluid sample with a predefined dosing rate to a person's nose by using the controllable fluid sample dispenser of claim 1, wherein the microdosing driver unit for selectively activating the microdosing device is implemented for receiving the control signals from a computer, a video game console, an interactive entertainment computer or a platform with an audio and/or visual media playing functionality.

30. Fluid sample dispenser, comprising:
a peristaltic micropump fluidically coupled to a fluid sample outlet, the microdosing device being configured to create, during an activation state of the peristaltic micropump, a flow of carrier gas directly to the environment at the fluid sample outlet, wherein the peristaltic micropump comprises a pump chamber providing a stroke volume for creating the flow of the carrier gas to the fluid sample outlet;
a fluid sample supplier fluidically coupled to a fluid sample reservoir, the fluid sample supplier being configured to selectively supply particles of the fluid sample from the fluid sample reservoir into the carrier gas flowing to the environment at the fluid sample outlet; and
a microdosing driver unit for adjusting a dosing rate of the fluid sample output the environment at the fluid sample outlet by selectively activating the peristaltic micropump and/or the fluid sample supplier for selectively supplying the fluid sample during the activation state of the peristaltic micropump to the environment at the fluid sample outlet,
wherein the microdosing driver unit is configured to adjust the dosing rate of the fluid sample output the environment at the fluid sample outlet based on the stroke volume of the peristaltic micropump and a number of pump strokes or diaphragm excursions for transporting the carrier gas in a predetermined direction to the fluid sample outlet, wherein the ratio of stroke volume and dead volume is greater than the ratio of delivery pressure and atmospheric pressure.

31. Fluid sample dispenser according to claim 30, wherein the fluid sample supplier comprises a further micropump comprising a pump chamber providing a stroke volume.

* * * * *